(12) United States Patent
Bhaskaran et al.

(10) Patent No.: US 7,641,925 B2
(45) Date of Patent: Jan. 5, 2010

(54) SYNERGISTIC COMPOSITION FOR THE TREATMENT OF DIABETES MELLITUS

(75) Inventors: Sunil Bhaskaran, Pune (IN); Vishwaraman Mohan, Pune (IN)

(73) Assignee: Indus Biotech Pvt. Ltd., Pune (IN)

( * ) Notice: Subject to any disclaimer, the term of this patent is extended or adjusted under 35 U.S.C. 154(b) by 191 days.

(21) Appl. No.: 11/356,274

(22) Filed: Feb. 15, 2006

(65) Prior Publication Data

US 2006/0153937 A1 Jul. 13, 2006

Related U.S. Application Data

(62) Division of application No. 10/846,299, filed on May 14, 2004, now Pat. No. 7,141,254.

(60) Provisional application No. 60/470,742, filed on May 14, 2003.

(51) Int. Cl.
*A61K 36/48* (2006.01)
*A61P 7/12* (2006.01)

(52) U.S. Cl. ........................ 424/757; 514/866

(58) Field of Classification Search ............... None
See application file for complete search history.

(56) References Cited

U.S. PATENT DOCUMENTS

| 5,470,879 | A | 11/1995 | Sauvaire et al. |
| 5,847,109 | A | 12/1998 | Garti et al. |
| 5,997,877 | A | 12/1999 | Chang |
| 6,495,175 | B2 | 12/2002 | Rao et al. |
| 6,692,777 | B2 | 2/2004 | Lee |

OTHER PUBLICATIONS

Al-Habori, M et al. Medicinal and Aromatic Plants—Industrial Profiles (2002); 11(Fenugree,), pp. 162-182. Pharmacological properties of fenugreek.*
Sharma et al. "Effect of fenugreek seeds on blood glucose and serum lipids in Type I diabetes." Article printed from the internet sit Pub Med (Jul. 22, 2004).
Fowden et al. "4-Hydroxyisolueucine from seed of Trigonella Foenum-Graecum." *Pytocheinistry*. vol. 12, pp. 1707-17011. (1973).
Alcock et al. "Stereochemistry of the 4-Hydroxyisolueucine from Trigonella Foenum-Graecum." *Pytochemisny* vol. 28, No. 7, pp. 1835-1841. (1989).
Van Loon et al. "Amino acid ingestion strongly enhances insulin secretion in patients with long-term type-2 diabetes." *Diabetes Care*, vol. 26, No. 3, pp. 625-630 (Mar. 2003).
McKee, H.S. et al. "Physiology of pea fruits. II Soluble nitrogenous constituents in the developing fruiit." *Austrian Journal of Biological Sciences*, vol. 8, pp. 467-475. (1955).
Ngudi, D. et al. "Cassava cyanogens and free acids in raw and cooked leaves." *Food and Chemical Toxicology*, vol. 41, No. 8, pp. 1193-1197. (2003).
Rozan, P. et al. "Free amnio acids present in commercially available seedlings sold for human consumption. A potential hazard for consumers." *Journal of Agricultural and Food Chemistry*, vol. 48, No. 3, pp. 716-723. (2000).

* cited by examiner

*Primary Examiner*—Michele C. Flood
(74) *Attorney, Agent, or Firm*—Merchant & Gould P.C.

(57) ABSTRACT

A synergistic composition for the treatment of diabetes in a subject in need thereof, comprising Trigonelline of concentration ranging between 20 to 30%, amino acids of concentration ranging between 20 to 60%, and soluble fiber of concentration ranging between 10 to 60%, optionally along with pharmaceutically acceptable additives, a process thereof and also, a method of treating diabetes.

12 Claims, 2 Drawing Sheets

SYNERGISTIC COMPOSITION FOR THE TREATMENT OF DIABETES MELLITUS

This application is a divisional of U.S. Ser. No. 10/846,299, filed May 14, 2004, which is the non-provisional of U.S. Ser. No. 60/470,742, filed May 14, 2003 and which application(s) are incorporated herein by reference. A claim of priority to both, to the extent appropriate is made

FIELD OF THE PRESENT INVENTION

The present invention relates to a synergistic composition for the treatment of diabetes mellitus, and also a process of preparing the synergistic composition.

BACKGROUND AND PRIOR ART REFERENCES

Diabetes Mellitus is the most common endocrine disease. This disease is characterized by poor regulation of blood glucose levels in human beings. Blood glucose is the source of energy for basic cell functions. This glucose is driven to the cell by insulin, which is secreted by the pancreas. Diabetes Mellitus is caused by inadequate insulin secretion by the pancreas or the resistance generated by insulin receptors to the insulin. Therefore, this disease is characterized by a metabolic abnormality. Diabetes is a major metabolic disorder in which the body does not produce or properly use insulin and is characterized by hyperglycemia, glycosuria, hyperlipidemia, negative nitrogen balance and sometimes ketonemia. Diabetes is one of the most common diseases affecting human population today.

In India, as per WHO reports, about 60 million people would be suffering from diabetes by the year 2025. This would put India as the #1 country in the world affected from this epidemic disorder. Diabetes among urban Indians has increased from 11.8% in 1995 to 13.2% in 2000. This disorder-strikes people during the most productive stage of their lives. Based on recent studies conducted and published, it appears that this disease is caused more by lifestyle and food habits than genetic predisposition for the disease. This is particularly true in urban areas wherein the lifestyle results in people exercising inadequately or tending to eat more processed, ready-to-eat food. This in turn has led to obesity and later, to the onset of diabetes. Diabetes Mellitus is not curable. Presently, this disorder is managed by taking popular drugs available in the marketplace. These drugs fall into the following categories:

i. Pancreatic stimulators:—This class of drugs helps to stimulate the pancreas, leading to increased secretion of insulin. This addresses the diabetes caused by inadequate insulin secretion.
ii. Insulin sensitizers:—This category of drugs improves the cell's sensitivity to the presence of insulin, thereby improving the uptake of glucose into the cells, leading to better blood sugar control.
iii. Insulin:—This is exogenously supplemented in the case of people suffering from both type I and type II diabetes.

As mentioned earlier, diabetes is a lifestyle disease and cannot be cured. The current therapies available therefore only offer a blood sugar management mechanism. As diabetes is a chronic, long-duration disease, these drugs need to be taken on a sustained basis. Currently, available synthetic drugs suffer from concomitant side effects caused due to long duration of usage. Literature survey indicates that cardiovascular mortality was higher in patients with oral hypoglycemics than in those treated with diet and exercise alone or with insulin. Sulphonylureas cause hypoglycemia as a side effect. Biguanides cause lactic acidosis. Oral hypoglycemia drugs also cause GIT irritation, weight gain, hypertension, etc. On continuous and constant exertion, the diabetic person is also liable for pancreatic fatigue. In addition, it is also seen that many of the existing drugs available lead to drug resistance in patients with long durations of use.

As mentioned earlier, the long-term complications of diabetes are more damaging. This is caused by spikes in blood sugar in patients during the day. Increased blood sugar even for short periods leads to glycosylation of Haemoglobin. And glycosylated Haemoglobin causes long-term irreversible damages to eyes, kidneys, nerves and blood vessels.

Complications of Diabetes:—A wide-spread pathological change is thickening of capillary basement membrane, increase in vessel wall matrix and cellular proliferation resulting in vascular complications like lumen narrowing, early atherosclerosis, sclerosis of glomerular capillaries, retinopathy, neuropathy and peripheral vascular insufficiency. The level of glycosylated hemoglobin (HbAlc) is also increased in diabetes and is taken as an index of protein glycoslyation. It reflects the state of glycaemia over the preceding 2-3 months. As such, there is no drug available for the treatment of diabetic complications. Consequently, the need of the hour is to develop safe and efficacious drugs that can help in the management of blood sugar in diabetes mellitus patients. This drug should lend itself for long-term use without any side effects and without developing resistance.

Ayurveda:—Ayurvedic literature refers to the usefulness of many plant extracts in the treatment of diabetes mellitus. In general, pharmacological studies over the last five decades have not brought out adequate effectiveness of such blood glucose lowering drugs. However, physicians in India who practice Ayurveda, Unani, and Siddha use extracts of leaves, flowers, fruits, seeds, wood, bark, roots, or even whole plants of more than a hundred Indian medicinal plants for the treatment of diabetes.

In Ayurveda, each herb has properties of curbing many disorders. Therefore, the crude extracts of herb have failed in offering clinically significant results in any single disorder. Comprehensive studies on the components of the herb that are responsible for certain indications need to be undertaken to obtain effective medications from this therapy.

Alternative approach/therapy for control and management of diabetes:—In recent years, efforts have been focused on increasing beta cell mass in diabetes through induction of islet neogenesis or pancreatic regeneration. In this context, the role of herbal remedies is highly significant. Ayurveda aims at treating the disease at the root level. Hence, it would be worth exploring the action of selected pure ingredients composition from herbs for their pancreatic viability enhancement and neogenesis potential.

Fenugreek is used to treat diabetes, migraines, allergies and elevated cholesterol in traditional medicinal practices in India. As per the ancient Indian practice of Ayurveda and Naturopathy, fenugreek seed is traditionally taken in a powdered form, or boiled with water, or as a sprouted seed for the control of blood sugar. It must also be noted that Fenugreek in India is used as a culinary spice and as a medicinal herb. In general, the varieties that are used for medicinal purpose have smaller grains, are dark brown in colour and bitter in taste when compared to the varieties used for culinary purposes. At present, there is no documented evidence of better medicinal property of the varieties used for medicinal purposes. Also, it appears that the medicinal effect of control of blood sugar obtained with the consumption of fenugreek seed is widely varying and cannot be relied upon as a reliable agent for control of blood sugar.

Clinical Studies:—Fenugreek seeds contain about 50% dietary fiber if used as a defatted powder. Similar to Guar Gum, fibers present in the seeds may slow gastric transit time. Slowing the rate and extent of glucose absorption in the gut is not likely to be the sole mechanism for hypoglycemic benefit. Sauvaire et al isolated an amino acid present in fenugreek seeds (4 Hydroxyisoleucine) that increases glucose-induced insulin release. Fenugreek seeds contain the alkaloid trigonelline, which has a hypoglycemic effect.

The following human studies demonstrate the role of fenugreek in both type 1 and type 2 diabetes therapy. Madar et al (U.S. Pat. No. 5,847,109) found that 17 of 21 patients with type 2 diabetes had a reduction in 2 hour postprandial serum glucose averaging 30 mg/dL following administration of 15 grams of ground fenugreek seed (these are approximate figures interpreted from a chart; numeric data were not given). Four patients had no significant change in post-prandial glucose measurements.

Sharma et al (European J. of Clinic Nutr Volume 44, Pages 301, 306, 1990) studied fenugreek in type 1 and type 2 patients using an interesting mode of delivery. Fenugreek powder was treated to remove the familiar taste, divided into two equal doses and incorporated into chapati, a type of unleavened bread. A serving of chapati was given with lunch and dinner. In a crossover, placebo-controlled trial with 60 type 2 patients, the treatment group received 12.5 mg defatted fenugreek powder in chapatis at lunch and dinner with isocaloric diets for 24 weeks. This trial found a significant decrease in the area under the curve for blood glucose concentration of 40.6% in the treatment group. A double blind study was conducted using isocaloric diets with or without defatted fenugreek powder in 10 patients with type 1 diabetes for two 10-day study periods. Five of the patients received fenugreek during the first 10 days and the rest received it during the second period. The fenugreek diet significantly reduced fasting serum glucose levels from 271.8±4.2 mg/dL to 196.2±49.5 mg/dL. After ingestion of a glucose load, serum glucose levels in the treatment group were reduced and the area under the curve for blood glucose concentration decreased significantly by 18.7%. Significant reductions in total cholesterol and triglycerides have been documented with the use of fenugreek.

Lessly Fowden, Helen Empratt and Alfred Smith of the Department of Botany and Microbiology, University College, Gower Street, London did a very detailed study of Fenugreek seed and identified an Amino Acid—4 Hydroxy Isoleucine in fenugreek seed. They published their findings in Phytochemistry, 1973, volume 12, page 1707 to 1711 under the title "4 Hydroxy Iso Leucine from seeds of Trigonella Foenum Graecum". This paper explains a detailed method for extraction & purification of 4 Hydroxy Iso Leucine from Fenugreek seeds. They have also explained a method for identification of this amino acid. They suggested ethyl alcohol & water extraction of ground seeds of amino acid followed by ion exchange separation. This crude extract as per their method was further purified & crystallized to give a pure compound of 4 Hydroxy Iso Leucine. Their structure elucidation was also explained in the above article.

In 1989, N. W. Alcock, David H, G Grocet et al of Department of Chemistry University of Warwick published a detailed paper in Phytochemistry Volume 23, page 1835 to page 1841 of 1989 titled "Stereochemistry for the 4 Hydroxy Iso Leucine from Trigonella Foenum Graecum".They used an extraction process as used by Lessly Fowden to get a pure compound of 4 Hydroxy Iso Leucine. They elucidated the structure correctly.

U.S. Pat. No. 5470879 of 1995 title "Treatment of Non-Insulin dependant Diabetes" by Sauvaire et al talk about 4 Hydroxy Iso Leucine for increasing insulin secretion in diabetic patients. Coincidently, the method of extraction and purification used in the patent is same as the one published by Lessly Fowden in 1973 in the prior art. This patent, however, discloses certain properties of 4 Hydroxy Iso Leucine in stimulation of the pancreas to increase insulin secretion. This patent studies the effect of 4 Hydroxy Iso Leucine in animals only. They have disclosed studies invitro in rat pancreas, invivo in experimental rats, experimental dogs and mice. There is no study done in patients suffering from diabetes mellitus.

Ingestion of Amino Acid:—Protein Mixture leads to a significant increase in the insulin secretion response to Type II Diabetes, Diabetes Care 2003 26, 625-630 by Dr. Luc J. C. Van L Maastricht University, Netherlands. The insulin response to carbohydrate consumption with Type II Diabetes is enhanced by administering free Amino Acid/Protein mixture. The Researchers examine the insulinotropic capacity of a mixture containing free Leucine and Protein in Diabetic Patients. They find that compared with carbohydrate ingestion alone, co-ingestion of the amino acid protein mixture led to significant insulin secretory response among Type II Diabetes. This is tripled as per the study.

U.S. Pat. No. 5,847,109 of 1998 title "Galactomannan products of compositions containing the same by Garti et al claim method for Isolation of Fenugreek Galactomanin & use as a nutraceuticals in reducing post—prandial glucose, insulin response & cholesterol levels. They have quoted results of a one-week study on 22 subjects for this claim. The quantity of fenugreek derived galactomanin administration to them was 10 grams.

U.S. Pat. No. 5,997,877 of 1999 by Peter Chang describes a process for the fractionation of Fenugreek seeds & extraction of the various fractions such as soluble dietary fibre, deflavoured fenugreek seed, high protein fenugreek meal, etc. There is no reference to any diabetic treatment.

U.S. Pat. No. 6,495,175 of 2002 by G. B. Rao et al describes 'a method for obtaining substantially pure fixed oil, Oleoresin & dietary fibre from fenugreek seeds. There is no mention of any diabetic treatment with any of these compounds.

The hypoglycemic effect of the alkaloid Trigonelline of fenugreek seed has been explained in the publication 'LANCET' 1967, 2 [7529] 1311—2 title 'Hypoglycemic effect of trygonelline by Mishkins KYJ, Joseph B, Suleman F G et al.

OBJECTS OF THE PRESENT INVENTION

The main object of the present invention is to develop a synergistic composition for treating diabetes.

Another main object of the present invention is to develop a process for the preparation of a synergistic composition from fenugreek seeds for treating diabetes.

Yet another object of the present invention is to develop a method of treating diabetes, using the synergistic composition obtained from fenugreek seeds.

Still another object of the present invention is to develop a method of treating diabetes, using Trigonelline.

SUMMARY OF THE PRESENT INVENTION

The present invention relates to a synergistic composition for the treatment of diabetes in a subject in need thereof, said composition-comprising Trigonelline of concentration ranging between 20 to 30%, amino acids of concentration ranging between 20 to 60%, and soluble fibre of concentration ranging between 10 to 60%, optionally along with pharmaceutically acceptable additives, a process thereof and also, a method of treating diabetes.

DETAILED DESCRIPTION OF THE PRESENT INVENTION

Figure 1:
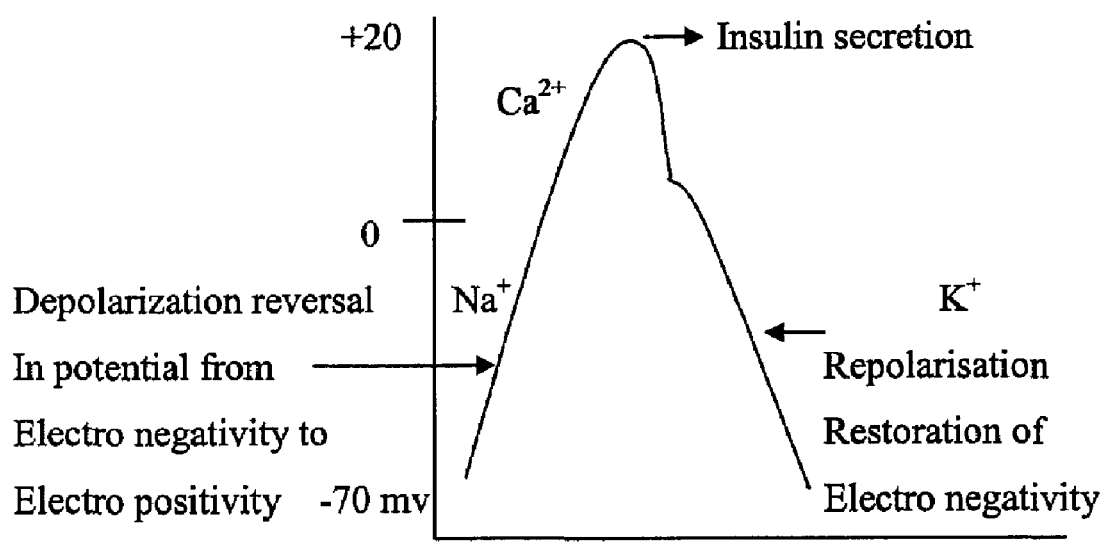
FIGS. 1 and 2 schematically illustrate depolarization, which means reversal change in transmembrane potential of cell by reducing conductance of ATP sensitive K+ channels. This enhances $Ca^{2+}$ influx, producing degranulation of β cell of pancreas. Thereby increasing rate of insulin secretion at any glucose concentration. Decreased K+ ion concentration indicates the repolarisation effect as the ATP dependant $I_{K-ATP}$.
Figure 2:
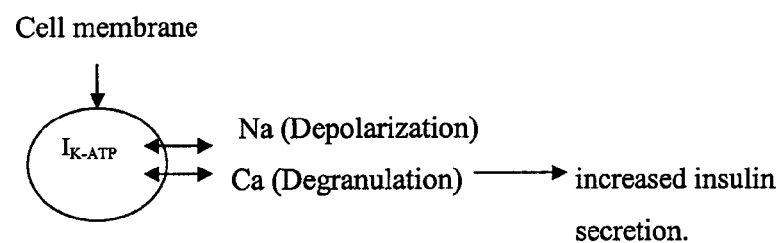

Accordingly, the present invention relates to a synergistic composition for the treatment of diabetes in a subject in need thereof, said composition-comprising Trigonelline of concentration ranging between 20 to 30%, amino acids of concentration ranging between 20 to 60%, and soluble fibre of concentration ranging between 10 to 60%, optionally along with pharmaceutically acceptable additives, a process thereof and also, a method of treating diabetes.

In still another embodiment of the present invention, wherein the invention relates to a synergistic composition for the treatment of diabetes in a subject in need thereof, said composition-comprising Trigonelline of concentration ranging between 20 to 30%, amino acids of concentration ranging between 20 to 60%, and soluble fibre of concentration ranging between 10 to 60%, optionally along with pharmaceutically acceptable additives.

In still another embodiment of the present invention, wherein the amino acids are selected from a group comprising L-arginine, Leucine, Isoleucine, and 4-Hydroxyisoleucine.

In still another embodiment of the present invention, wherein the soluble fiber is galactomannan.

In still another embodiment of the present invention, wherein the additives are extracted from the same fenugreek which comprises of a group containing galactomannan.

In still another embodiment of the present invention, wherein the diabetes is Type II diabetes.

In still another embodiment of the present invention, wherein the composition is obtained from plant Fenugreek.

In still another embodiment of the present invention, wherein the composition is free of adverse effects.

In still another embodiment of the present invention, wherein the invention relates to a process for the preparation of a synergistic composition from plant fenugreek comprising Trigonelline of concentration ranging between 20 to 30%, amino acids of concentration ranging between 20 to 60%, and soluble fibre of concentration ranging between 10 to 60%, optionally along with pharmaceutically acceptable additives, said process consisting steps of:

flaking fenugreek seeds,
extracting the flaked seeds with hydro-alcohol,
concentrating the extract under vacuum to remove alcohol,
extracting the concentrate with n-hexane to remove fats and lipids,
diluting the defatted concentrated,
filtration of the diluted extract to remove insolubles to obtain resultant,
filtering the resultant through column chromatography to elute amino-acids, and Trigonelline, and
adding fibre of fenugreek into the amino acids and Trigonelline to obtain the synergistic composition.

In still another embodiment of the present invention, wherein the extraction is at temperature ranging between 20 to 70° C., preferably 35° C.

In still another embodiment of the present invention, wherein the flakes are of size of about 15mm.

In still another embodiment of the present invention, wherein hydro alcohol is isopropyl alcohol and water in equal ratio.

In still another embodiment of the present invention, wherein the extraction is for time duration ranging between 3 to 24 hours, preferably 12 hours.

In still another embodiment of the present invention, wherein the amino acids are selected from a group comprising L-arginine, Leucine, Isoleucine, and 4-Hydroxyisoleucine.

In still another embodiment of the present invention, wherein the column chromatography is Ion exchange chromatography.

In still another embodiment of the present invention, wherein the fibre is Galactomannan.

In still another embodiment of the present invention, wherein the invention relates to a method of treating diabetes in a subject in need thereof, said method comprising step of administering pharmaceutically acceptable amount of composition comprising Trigonelline of concentration ranging between 20 to 30%, amino acids of concentration ranging between 20 to 60%, and soluble fibre of concentration ranging between 10 to 60%, optionally along with pharmaceutically acceptable additives, to the subject.

In still another embodiment of the present invention, wherein administration of the synergistic composition is at dosage ranging between 50 to 2000 mg/kg body weight.

In still another embodiment of the present invention, wherein method shows hypoglycemic effect of about 50%.

In still another embodiment of the present invention, wherein the method shows about 300% increase in the viability of the islets.

In still another embodiment of the present invention, wherein the method maintains the morphology of the pancreatic cells.

In still another embodiment of the present invention, wherein the synergistic composition is administered orally.

In still another embodiment of the present invention, wherein the synergistic composition acts at the pancreas through potassium channel mediated insulin secretion.

In still another embodiment of the present invention, wherein the invention relates to a method of treating diabetes in a subject in need thereof, said method comprising step of administering pharmaceutically acceptable amount of Trigonelline, amino acids and galactomannan fibers, optionally along with pharmaceutically acceptable additives, to the subject.

In still another embodiment of the present invention, wherein the additives are extracted from the same fenugreek which comprises of a group containing galactomannan.

In still another embodiment of the present invention, wherein the diabetes is type II diabetes.

In still another embodiment of the present invention, wherein the composition is free of adverse effects.

In still another embodiment of the present invention, wherein the invention relates the administration of the synergistic composition is at dosage ranging between 50 to 2000 mg/kg body weight.

In still another embodiment of the present invention, wherein the method shows hypoglycemic effect of about 35%.

In still another embodiment of the present invention, wherein the method shows about 300% increase in the viability of the islets.

In still another embodiment of the present invention, wherein the method maintains the morphology of the pancreatic cells.

In still another embodiment of the present invention, wherein Trigonelline, amino acids and galactomannan fibers, is administered orally.

In still another embodiment of the present invention, wherein Trigonelline, amino acids and galactomannan fibers act at the pancreas through potassium channel mediated insulin secretion.

The instant invention is not only novel but also, inventive in nature. The comparative results of fenugreek seed powder (whole), and the composition of the instant application are shown below to establish inventiveness of the application.

| Material | % decrease in glucose level |
| --- | --- |
| Fenugreek seed powder | 18% |
| Composition of the instant Application | 51% |

The aforementioned table clearly shows that the inventors have been able to reach the right combination of selective components of the fenugreek. In addition, the right combination is further supported by the inventiveness in using appropriate concentration ranges of each of the three components of the composition. This makes the invention both novel and inventive in nature.

Further, the activity analysis of all the components of fenugreek showed very interesting data. The activity was restricted to only a couple of components. Also, synergy was observed by a selective combination of three components of the composition. The same is elaborated with the help of experimental data as given below.

| Components of fenugreek | Hypoglycemic activity (%) |
| --- | --- |
| Volatile flavor compounds | 0 |
| Fixed oils | 0 |
| Soluble fibers | 0 |
| Trigonelline | 31 |
| Saponin | 0 |
| Amino acids | 8% |
| Composition of the instant application | 51% |

The aforementioned results clearly establish synergy of the composition. The activity is much more that the mere additive effect of individual components. Rather, it is very clearly reflected in the data that the non-active components are bringing down the activity of the active components. Therefore, elimination of the inactive components led to significant increase in the overall activity.

Apart from the synergy as observed in the invention, the composition leads to increase in the pancreatic beta cell mass increase in a subject. This is a novel aspect of the invention.

There is no other data available in accordance to our knowledge, wherein the beta cell mass increase is been attained. This provides an indication of physiological significance of instant composition. In addition, there is an increase of about 300% in the viability of the islets. Thus further supplements the physiological changes required to provide a holistic benefit to a subject in thereof.

Thus, the composition is not only effective in new cases of diabetes mellitus, but also, would be effective in management of patients with resistance to other generation 1, 2, and 3 drugs.

Therefore, the patentability requirements of novelty, inventiveness, and utility are satisfied. The current method of management of blood sugar in diabetes mellitus does not lend itself for long-term use due to side effects. Long-term complications of Diabetes are also well known and there are no effective remedies for them. Therefore, there is always a need for development of new compounds for the management of blood sugar.

Fenugreek Seed is known to possess anticholesterol and antidiabetic activities. However the compounds responsible for effective antidiabetic properties have not been clearly elucidated and studied in detail in human subjects. Fenugreek Seed contains, among other, several compounds such as:
1. Host of Amino Acids
2. Volatile flavor compounds
3. Fixed oils
4. Soluble fibers like galactomannan
5. Trigonelline
6. Various Saponins Apparently some of these in combination are responsible for antidiabetic properties and some others in combination are responsible for lipid lowering qualities.

Earlier studies cited in this patent refer to seed powder and seed fibers administered in large quantities to obtain some glycemic control. However, the level of control demonstrated is not good enough to offer clinically significant glycemic control, which can be taken advantage of by subject suffering from type 2 diabetes.

An amino acid (4 Hydroxyisoleucine) found in the seed has a property to increase insulin secretion in glucose mediated way. This has been tested extensively in animals. However there is no study done in human subjects suffering from diabetes type 2 to understand the impact of this amino acid in the management of this type 2 diabetes along with safety for long-term administration.

It is known from published studies that certain amino acids like Leucine improves insulin secretion response among type 2 diabetes. They have not assumed the role of mainstream medication as yet. Perhaps, this branched chain amino acid (4 Hydroxyisoleucine) behaves in a manner similar to Leucine.

The present invention is about identification of individual compounds of Fenugreek seed that have beneficiary effect in the case of type 2 diabetes. The present invention illustrates the method for extraction of a compound from Fenugreek seed, resulting in a combination of certain molecules that act in tandem and with synergy and leads to effective control of blood glucose in subjects suffering from type 2 diabetes. The present invention explains the composition of matter of the extract derived from Fenugreek seed.

The varieties that have high biological activities in mice were identified and subjected to extraction to understand individual compounds present. It is found that these varieties are rich in:
1. Amino acids
2. Trigonelline
3. Soluble Fiber galactomannan.

The amino acids found in this seeds are L-arginine, leucine, isoleucine and 4-Hydroxyisoleucine. It was decided to work with seed screened for optimal activity. Thin layer chromatographic method was developed to screen for amino acids and Trigonelline. A quantitative method was developed for checking soluble fiber.

It was decided to work with the seeds whose ratios were optimum, after establishing the amino acids content and Trigonelline content by TLC methods.

The seeds were subjected to flaking and hydro alcohol extraction at temperatures ranging from 20° C. to 70° C. and alcohol composition ranging from 50% to 90% (the remaining being de-mineralized water) for a period ranging from 3 hours to 24 hours, preferably about 12 hours. The clear, filtered extract is concentrated to a predefined volume so as to remove maximum alcohol and diluted to a predetermined volume with water. The resulting solution is subjected to fine filtration followed by Ion exchange chromatography. The process of known prior art of ion exchange chromatography was used except for the selection of the ion exchange resin, which can bind both Trigonelline as well as amino acids completely and the resin selection was made in such a way that the compounds eluted in the same medium without leaving any traces on the resin.

The elutes were again passed through another weak acid Cation exchange resin in $H^+$ form to selectively remove the metabolites and impurities formed during the isolation, concentration and elution process. This part exclusively removes the smelly cyclisation products of 4 Hydroxy Isoleucine and the Keto-methyl 4 Hydroxy valeric acid.

The resultant elute contained only amino acids and Trigonelline. The liquor obtained was spray dried on co-current equipment having a disc atomizer with a speed of 30,000 rpm.

The resultant powder was in a fine granular form, which can be readily formulated after standardization.

In the above-mentioned process, the ratio of the active biomolecules, which were present in the original form i.e. seed, was maintained in totality in the finished product. This was an important criterion for the activity of the said composition.

The said formulation, after mixing with suitable carriers (preferably the Fenugreek fiber as the carrier), was subjected to animal studies as well as human studies on diabetic subjects having very high glycosylated Haemoglobin values.

EXPERIMENT 1

After screening the seeds for the presence of total amino acids and Trigonelline using Thin Layer chromatography on a pre-coated Silica gel TLC plate using n-Butanol: Acetic acid: water in the ratio of 12:8:2 and initial scanning using uv at 254 nm for the presence of Trigonelline. Ninhydrin colour development was used for total amino acid presence.

The selected seeds in a quantity of 1 Kg were flaked in a flaker to expose the inner core, resulting in flakes of average 15 mm in size. These flakes were than subjected to Hydro alcohol extraction using 6 litres of Isopropyl alcohol:water mixture in the ratio of 50:50 at 35° C. for 12 hours. The resultant liquid (about 5500 ml) was concentrated to a final volume of 150 ml under vacuum at 45-50° C. This liquid was extracted with 3×50 ml of n-Hexane to remove fats and lipids. The defatted concentrate was diluted with de-mineralized water to a final volume of 500 ml. This liquid was then subjected to fine filtration through 200-mesh size screen to remove insolubles.

The filtered liquid was then passed through a glass column of 500 mm length×25 mm diameter containing 100 ml of strong acid Cation exchange resin in $H^+$ form, freshly regenerated with 600 ml of 3% HCL in water, followed by washing to neutral pH. After passing the liquid, the column is washed with de-mineralized water to neutral pH. The loaded amino acid and Trigonelline were eluted out with 200 ml of 0.5 N ammonia solution. The ammonia liquid is circulated in the column until it attains a stable pH of about 8.0

The resultant solution was then passed through a glass column of 800 mm length×25 ml diameter containing 200 ml of freshly regenerated weak acid Cation resin in gel form. The eluent from this column is a colourless, neutral liquid having only compounds such as amino acids and Trigonelline present in the ratio as in the mother seed. This product is spray dried in the following conditions:

| | |
|---|---|
| Air flow: | Co-current |
| Inlet Temperature: | 165° C. |
| Outlet Temperature: | 85° C. |
| Atomizer revolution: | 30,000 rpm |

The resultant granule from the spray drying process was found to be free flowing and suitable for formulation.

The resultant powder is screened in HPLC for amino acids by derivatization method using DNFB (Dinitro Flouro Benzene) and Trigonelline using WV. This contains total amino acids in the ratio of 20 to 60%, Trigonelline from 20 to 30% and soluble fiber (Galoctomannen) 10 to 60%.

EXPERIMENT 2

A Spray dried extract of Fenugreek as explained in Experiment 1 is taken. This is filled into 00 size capsules after mixing with an excipient. The excipient is the fiber extracted from fenugreek seed. The fiber is extracted from the waste of the fenugreek seed after the extraction of the compound containing total amino acids and Trigonelline. The extraction procedure for the fiber is as below:—

The waste of fenugreek seed is boiled with 5-10 times its volume of de-mineralized water for 2 to 3 hours at a temperature of 70-80° C. This is subjected to coarse and fine filtration. The filtered liquid is treated with activated charcoal to remove the coloring matter. This liquid is vacuum concentrated to $\frac{1}{3}^{rd}$ its original volume. To this is added an alcohol to precipitate the fiber. The precipitate is filtered to obtain the fiber residue. The fiber residue is dried and ground to a fine powder. The powdered fiber mainly contains the complex sugar from the seed in the form of Galactomannan.

The excipient and the active drug as extracted in Experiment No. 1 are mixed in such a way as to get a composition of total amino acids in the ratio of 20 to 60%, Trigonelline from 20 to 30% and soluble fiber (Galoctomannen) 10 to 60%.

EXPERIMENT 3

A dose response study for the test drug was conducted in healthy wistar rats weighing about 100-150 Gms. 96 rats, which were divided into 6 equal groups, were given the test drug in different doses ranging from 250 mg/kg, 500 mg/kg, 1000 mg/kg and 2000 mg/kg, with a group kept as control rats not receiving the test drug. On the basis of this experiment, it was found that administration of a single dose of test drug at 500 mg per Kg, 1 gm/kg and 2 gms/kg produced hypoglycemic effect. The onset of action was 4 hours after administration for 500 mg per Kg, 3 hours after administration of 1 gm/kg and 1 hour after the administration of 2 gms/kg of test drug. The duration of action was 4 hours for 500 mg per Kg, 7 hours for 1 gm/kg of drug and 24 hours for 2 gms/kg of the drug dose. This experiment demonstrated that the drug had a good hypoglycemic effect of about 20% at a dose of 1 gm/kg in the case of healthy wistar rats. Also, administration of 1 gm/kg of test drug for 15 days showed reduction in blood sugar level from 96.33 to 78 mgm percentage. The blood lipid profile was not altered remarkably.

EXPERIMENT 4

Sub-acute toxicity for this test drug was conducted in Swiss wistar rats of either sex having weights of 150- 250 gms. 4 groups of 8 animals each were classified, with 1 as control group, and the remaining were drug treated at dosage levels 1 gm/kg body weight, 2 gm/kg of body weight and 4 gm/kg of body weight.
1. These groups were administered drugs for a period of 15 days continuously and monitored for the following:
   Body weight
   Food consumption
2. At the end of the trial, they were sacrificed and the organs liver, kidney, lungs, spleen and stomach were taken for histopathalogy and organ weight checking.
3. Tests like kidney function test and liver function tests were performed in all the animals.
4. Effects of the drug on hematology parameters such as hemoglobin, RBC count, WBC count, Neutrophils, Lymphocyte, Eosinophils and Erythrocite sedimentation rate were performed.
5. On the basis of the above studies, it has been observed that the net gain in body weight of drug treated animals was similar to that of the control. The food consumption of the drug treated groups compared well with the control group.
6. The administration of the drug did not show any significant difference in the hematology parameters as compared to the control group.
7. The drug at all 3 levels of administration did not cause any kidney toxicity in rats.
8. The liver function test indicated normal liver function.
9. The organ weights did not show any variation and compared well with the control group.
10. Histopathology of the internal organs reveal no abnormality in the liver, kidney, spleen, stomach and lungs. On the basis of this toxicity study, it is concluded that the drug is safe in rats at the doses administered.

EXPERIMENT 5

16 mice were induced diabetes by the administration of Alloxan. By conducting blood test on these animals, they were confirmed to have high blood sugar levels. After confirmation of diabetic induction, they were treated with the test drug at the dose of 2 gm/kg of the body weight for a period of 21-26 days. This time period was decided by the reversal of the sugar content in the urine of the mouse. The sugar content of the urine was tested everyday. The mice tested positive initially. By $21^{st}$-$26^{th}$ day, the blood sugar in the urine tested negative during treatment with the drug. At the end of the treatment, the animals were sacrificed and their pancreas extracted for further studies. At this time, the blood samples were also taken for blood sugar check. The pancreas was subjected to large-scale isolation of islets by the standard procedure elucidated in the article "Large Scale Isolation of Islets"by Tissue Culture of Adult Mouse Pancreas by Y. M. Shewade, M. Umrani and R. R. Bhonde as published in Transplantation Proceedings, 31, 1721-1723 (1999). Isolated islets were studied to check their viability. On the basis of this experiment, it was found that the blood sugar level of mice increased to 300-320 by the $3^{rd}$ day after the administration of Alloxan. The control group, which was not given the drug, showed a blood sugar of 480 by the $15^{th}$ day. Many mice in this group died during the study. Whereas, the drug treated animals at the dose of 2 gm/kg of body weight showed a decrease in the blood sugar level to 210 mgms. After the isolation and tissue culture of the islets as per the procedure, it was observed that the viability of the islets increased from 22% to 81%. The observations are tabulated below:

| RESULTS OF PANCREATIC CELL STUDIES | | | |
|---|---|---|---|
| ISLETS | CONTROL | ALLOXAN | ALLOXAN + DRUG |
| Morphology | Intact well defined | Distorted | Intact well defined |
| Number | 1135 ± 75.2 | 130 ± 5.1 | 780 ± 16.3 |
| Diameter | 104.6 ± 5.72 | — | 92.7 ± 4.32 |
| Area | 12775 ± 1160.5 | — | 11275 ± 110.3 |
| Viability | 92.3 ± 1.3 | 22.1 ± 3.3 | 81.3 ± 5.6 |

1. Islets are completely distorted and damaged in Alloxan group Mice.
2. Islets are mature, big and nearly opaque in control mice (No Alloxan, No Drug).
3. Islet size is smaller in Alloxan and drug group. The islets are translucent indicating there is repair and neogenesis.

This experiment proves that continued administration of the drug reverses diabetes in the case of mice that have been induced diabetes with alloxan. The drug is leading to improvement in viability of beta cells. This mechanism of action may help in restoring viability of damaged pancreas of type 2 diabetes. The pancreatic viability enhancement and pancreatic neogenesis potential are demonstrated in this experiment.

EXPERIMENT 6

The effect of the composition prepared as per Experiment 1 & 2 as well as their individual components separated on column chromatography were studied on normal Swiss Albino mice (male) in the weight range of 25-30 gms for GTT. The animals were fed in the following manner.
1) Administration of 2gm/kg of glucose by Inter Peritonially.
2) Administration of the drug (Orally):

| | |
|---|---|
| Total amino acids | 10 mg/kg |
| Trigonelline | 75 mg/kg |
| Hypoglycemic agent (Glyburide) | 10 mg/kg |
| Composition derived from Experiments 1 & 2 | 30 mg/kg |

3) Measurement of BSL at 0 minutes & 1 hour.
4) Immediately after blood removal at 1 hour, the animals were sacrificed by tail flicking and the pancreas was removed and homogenized using tris buffer. After centrifugation, the homogenate was characterized by thin layer chromatography and $K^+$ Ions by Biolyte analyser. Following are the observations:

ANIMAL STUDY ON MICE

| Description | Identification Mark on the Animal | Weight (in grams) | Sex | BSL at 0 hrs (mg/dl) | BSL after 1 hour (mg/dl) | K+ Ions (μMol) |
|---|---|---|---|---|---|---|
| Normal | FH | 29 | Male | 398 | 239 | 27.6 |
| Glyburide | HB | 29 | Male | 365 | 251 | 22.5 |
| Total Amino Acids | HBT | 28 | Male | 372 | 340 | 19.8 |
| Trigonelline | BT | 28 | Male | 341 | 233 | 21.8 |
| Drug Composition (Derived from Expts. 1 & 2) | Blank | 28 | Male | 404 | 200 | 18.3 |

The above experiment clearly indicates the enhanced activity of the composition made by the experiments as compared to the individual bio-actives. This demonstrates synergy of action in the composition. This experiment also demonstrates a possible mechanism of action for the composition.

Potassium channels

Ion channels consist of protein molecules designed to form water filled pores that cover the membrane and they can switch between open and closed states. Ion channels are selective and have gating properties i.e., the mechanism that controls the transition between open and closed states of the channel.

Many drugs act through ions. Oral antidiabetic drugs like sulphonylurea stimulate release of insulin from pancreas. They act on receptors on pancreatic β cell membrane. As a result of combination of sulphonylurea with receptors, there is depolarization, which means reversal change in transmembrane potential of cell by reducing conductance of ATP sensitive k+ channels. This enhances ca2+ influx, producing degranulation of β cell of pancreas.

Thereby increasing rate of insulin secretion at any glucose concentration.

Decreased K+ ion concentration indicates the repolarisation effect as the ATP dependant $I_{K-ATP}$.

EXPERIMENT 7

A prospective uncontrolled Pilot study to assess efficacy and safety of (TEST DRUG) composition derived from Experiments 1 & 2 in patients with Type II Diabetes Mellitus on treatment with Insulin. This type of patients were selected due to the viability enhancement/ neogenesis potential exhibited in mice studies Objectives:

The primary objectives of the study were to assess effect of TEST DRUG on fasting blood sugar levels (BSL) of Type II diabetic patients, who were on treatment with insulin and to assess the safety. Secondary objectives were to check effects of TEST DRUG on post-prandial BSL, glycosylated Hb to verify whether the dosage of insulin can be reduced after administration of TEST DRUG.

Study Design:

This clinical trial was a prospective, uncontrolled, multi centered study.

Study Population:
    30 patients
    Type II diabetes mellitus
    Fasting BSL between 100-140 mg/dl
    Taking insulin for at least last 6 months
    Stable BSL for last 8 weeks
    Stable dose of insulin for last 8 weeks Methodology:

Patients were screened for eligibility at −2 and 0 weeks. Eligible patients received TEST DRUG capsules. Treatment period was 24 weeks. Clinical and laboratory evaluation was done at 0, +2, +4, +6, +8, +12 +16 and +24 weeks.

Treatment Details:
    Product: TEST DRUG
    Pharmaceutical form: Capsule
    Subjects were asked to take 6 capsules per day in 3 divided doses. Each capsule weighing 700 mg Criteria for Evaluation of Efficacy:

Efficacy of TEST DRUG was assessed on the basis of reduction in fasting and PP BSL, glycosylated Hb, number of hypoglycemic attack between two consecutive visits, insulin dose after administration of the test drug compared to base line levels.

Criteria for Evaluation of Safety:

Safety criteria included adverse events, laboratory parameters, vital signs, physical examination and ECG examination Statistical Method:

Mean blood sugar levels of at different visit were compared with baseline by using Paired t test.

Efficacy Results:
1. Fasting blood sugar and post prandial blood sugar remained stable even after reduction in Insulin administered
2. Glycosylated Hb levels at V4 (Visits 4 week), V6 and V8 were compared with that of the base line. Statistically significant reduction was observed at V6 and V8
3. Mean requirements of insulin (in terms of units consumed per day) at various visits were compared with that of the base line. Statistically significant reduction in requirement of amount of insulin was observed at all visits.
4. Hypoglycemic attacks between two successive visits were compared with that of first two base line visits. Statistically significant increase in number of hypoglycemic attacks was observed at V3 and onwards.

Safety Results: There was no serious adverse event.

Based on this study for 6 month, it is proved that the drug is able to control blood glucose level very effectively in type 2 diabetes patients who do not respond to oral hypoglycemic agents. This drug is also effective in controlling glycosilated haemoglobin content in type 2 diabetes patients This indicates effective control in managing long term complications of diabetes.

The composition has a property of increasing the beta cell mass and stimulating the beta cell to secrete insulin, thereby increasing the viability of beta cells and enhancing the activity of diseased pancreas.

The composition has a property of synergistically working together to better control blood, sugar as compared to the effect of individual components.

The composition acts at the pancreas through potassium channel mediated insulin secretion The composition controls the fasting blood sugar in type 2 diabetes patients who do not respond to oral hypoglycemic agents and who are stabilized on insulin The composition controls the post prandial blood sugar in type 2 diabetes patients who do not respond to oral hypoglycemic agents and who are stabilized on insulin The composition creates reduction in the dose of insulin in type 2 diabetes patients who do not respond to oral hypoglycemic agents and who are stabilized on insulin The composition controls the glycosylated haemoglobin in type 2 diabetes patients who do not respond to oral hypoglycemic agents and who are stabilized on insulin The composition with its properties of glycosilated haemoglobin, fasting blood sugar, post prandial blood sugar, pancreatic beta cell mass enhancement and beta cell viability enhancement leads to better control of blood sugar and thereby delays the onset of long-term diabetic complications of retinopathy, nephropathy and neuropathy in type 2 diabetes patients who do not respond to oral hypoglycemic agents and who are stabilized on insulin

The invention claimed is

1. A method of treating diabetes in a subject in need thereof, said method comprising administering to the subject an effective amount of composition comprising:
   trigonelline of concentration ranging between 20 to 30%,
   amino acid of concentration ranging between 20 to 60%, and
   soluble fiber of concentration ranging between 10 to 60%, wherein the trigonelline, amino acid, and soluble fiber are from fenugreek;
   and optionally, pharmaceutically acceptable additive.

2. The method of claim 1, wherein the amino acid is selected from the group consisting of L-arginine, Leucine, Isoleucine, 4-Hydroxyisoleucine, and mixtures thereof.

3. The method of claim 1, wherein the soluble fiber comprises galactomannan.

4. The method of claim 1, wherein the pharmaceutically acceptable additive is extracted from fenugreek and comprises galactomannan.

5. The method of claim 1, wherein the diabetes is type II diabetes.

6. The method of claim 1, wherein administering the composition results in no adverse effects.

7. The method of claim 1, wherein administering comprises administering the composition at a dose of 50 to 2000 mg/kg body weight.

8. The method of claim 1, wherein administering the composition results in a hypoglycemic effect of about 51%.

9. The method of claim 1, wherein administering the composition results in about 300% increase in viability of islets.

10. The method of claim 1, wherein administering the composition maintains morphology of pancreatic cells.

11. The method of claim 1, wherein administering the composition is oral.

12. The method of claim 1, wherein administering the composition acts at the pancreas through potassium channel mediated insulin secretion.

* * * * *